United States Patent [19]

Ohfune et al.

[11] Patent Number: 4,803,292
[45] Date of Patent: Feb. 7, 1989

[54] PROCESS FOR PRODUCING STATIN AND RELATED COMPOUNDS

[75] Inventors: Yasufumi Ohfune; Masahiro Sakaitani, both of Osaka, Japan

[73] Assignee: Suntory Limited, Osaka, Japan

[21] Appl. No.: 93,271

[22] Filed: Sep. 4, 1987

[30] Foreign Application Priority Data

Sep. 4, 1986 [JP] Japan .................. 61-208573

[51] Int. Cl.$^4$ .................... C07C 125/065
[52] U.S. Cl. .................... 560/29; 560/160
[58] Field of Search ............... 560/29, 160

[56] References Cited

U.S. PATENT DOCUMENTS 4,397,786 8/1983 Evans et al. ............ 260/404
4,681,972 7/1987 Kaltenbronn et al. ............ 560/29

FOREIGN PATENT DOCUMENTS 0202736 11/1986 European Pat. Off. ............ 560/160
231695 11/1985 Japan .

OTHER PUBLICATIONS

Journal of Antibotics, 1970, vol. 23, pp. 259-363.
Nature, 1983, vol. 303, pp. 81-84.
Journal of Medicinal Chemistry by Rich, D. H., 1985, vol. 28, pp. 263-273.
Translation of 106th Meeting of Japanese Pharmaceutical Assoc., p. 208, issued Mar. 10, 1986.
Journal of Medicinal Chemistry, 1980, vol. 23, pp. 27-33.
Journal of Antibiotics, by H. Morishima et al., 1973, vol. 26, pp. 115-17.
Journal of Organic Chemistry, by W. S. Liu, 1978, vol. 43, p. 754.
Tetrahederan Letters, by P. W. K. Woo, vol. 26, p. 2973.

*Primary Examiner*—Paul Lieberman
*Assistant Examiner*—Hoa Van Le
*Attorney, Agent, or Firm*—Cushman, Darby & Cushman

[57] ABSTRACT

This invention relates to a process for producing statin having the general formula (I):

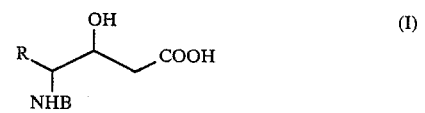

and related compounds thereof; (wherein R is a C1 to C6 alkyl group, a phenyl group or a C7 to C8 phenylalkyl group and B is a protective group for an amino group).

Recently, the anti-hyproperties of statin, namely the renin inhibitive properties, are attracting general attention.

8 Claims, No Drawings

PROCESS FOR PRODUCING STATIN AND RELATED COMPOUNDS

This invention relates to a process for producing protected statin and related compounds thereof having the general formula (I):

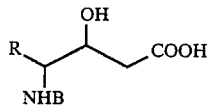

(wherein R is a C1 to C6 alkyl group, a phenyl group or a C7 to C8 phenylalkyl group and B is a protective group for an amino group).

By removing the protective group B of the compound of the formula (I), statin having the general formula (II):

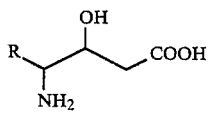

(wherein R is isobutyl) and the related compounds thereof may be obtained.

Statin having the following formula:

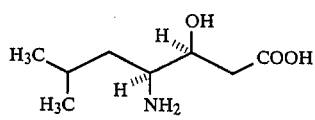

and a phenyl analog thereof, namely 4-amino-3-hydroxy-5-phenylpentanoic acid, hereafter abbreviated to AHPPA, having the general formula:

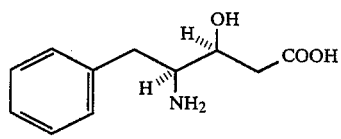

represents a constituent amino acid of a peptide obtained as natural bacterial metabolite which acts an inhibitor for aspartic proteinase. It is presently contemplated that this form of statin could be used as a medicament, especially as a hypotensive drug.

Above all, the peptide with statin and AHPPA introduced therein has been found to be useful as a hypotensive agent having strong renin inhibitive properties.

Statin was discovered by Umezawa, et al as a most critical amino acid constituting pepstatin (Journal of Antibiotics, 1970, vol. 23, page 259). Recently, the antihypertensive properties thereof, namely the renin inhibitive properties, are attracting general attention.

The hypotensive action is described, for example, in Boger's Nature, 1983, vol. 303, page 81 and *Journal of Medicinal Chemistry* by Rich, D. H., 1985. vol. 28, page 283. Attempts have also been made by a work group of Merck Company to use statin-containing synthetic peptide as a hypotensive drug (see Japanese Laid-Open Patent Publication Nos. 153345/1984 and 231695/1985).

The aforementioned AHPPA which is a phenyl analog was also found by Ohmura, et al from a natural source (see prereports for the 106th meeting of the Japan Pharmaceutical Association, page 208, issued on March 10, 1986).

The process for producing this AHPPA was described by D. Rich, et al in the Journal of Medicinal Chemistry, 1980, vol. 23, page 27. The synthesis of statin was reported in, for example, the Journal of Antibiotics, by H. Morishima, et al., 1973, vol. 26, page 115; in the Journal of Organic Chemistry, by W. S. Liu, 1978, vol. 43, page 754, and in the Tetrahedron Letters, by P. W. K. Woo, vol. 26, page 2973.

However, no inexpensive and industrially applicable process for producing optically active statin and AHPPA has so far been found.

The present inventors have directed their attention to the role of unusual naturally existing amino acids and have conducted research into a simple process for synthesis of the optical monomers thereof. In the course of these investigations, a new process for deriving 1,2- and 1,3-assymmetry has been arrived at.

Thus, by using the amino acid that is readily produced by using the newly found 1,2-assymmetry derivation reaction as the starting material, the present inventors have found a process for efficient synthesis of an amino hydroxyl compound such as protected statin. The present invention has been made on the basis of this finding.

In accordance with the present invention, there is provided a process for producing protected statin and related compounds thereof having the general formula:

(wherein R is a C1 to C6 alkyl group, a phenyl group or a C7 to C8 phenylalkyl group and B a protective group for an amino group) characterized by the steps of treating a silyl carbamate derivative having the formula

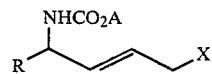

(wherein A is a t-butyldimethylsilyl or t-butyldiphenylsilyl group; X is a bromine atom, a chlorine atom, paratoluensulfonyloxy or methanesulfonyloxy group; and R is as defined above)

with a fluorine-containing ionic reagent in the presence of a null-valent or di-valent palladium and a trivalent organic phosphorus compound to produce a cyclic carbamate derivative having a general formula

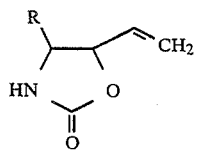

(wherein R has the meaning defined above);
subjecting said derivative to a hydroboronating reaction, basic oxidative cracking and protection of the amino group to produce a diol derivative having the general formula:

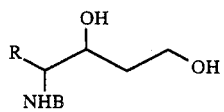

(wherein R has the meaning defined above and B a protective group for amino group);
and further oxidizing said diol derivative.

The present inventors previously found that, when amino acids including a t-butyldimethyloxycarbonyl group, herein abbreviated to Boc, a benzyloxycarbonyl group, herein abbreviated to Z, or an aryloxycarbonyl group, that are protective groups for amino groups extensively used in the field of amino acids or peptide chemistry, are acted on by t-butyldimethylsilyl triflate, herein abbreviated to TBDMSOTf, or by a palladium catalyst and t-butyldimethyl silane, a N-t-butyl dimethyl silyloxy carbonyl compound is obtained [see Sakaitani and Ohfune, Tetrahederon Letters, (1985), page 5543, 1986, page 3753.]. Taking an example of using BOC and TBDMSOTf, the reaction may be shown by the following reaction formula:

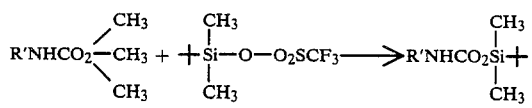

This means that the N-urethane type protective group has been captured as the N-carboxilate ions without concurrent de-carbonatation. The produced N-silyl ester reproduces N-carboxylate ions on processing with fluorine ions (see Sakaitani and Ohfune, Tetrahydron Letters, 1985, page 5543).

The most significant feature of the present invention is that, when reproducing the aforementioned N-carboxylate ions, processing with fluorine ions is performed in the presence of di- or null-valent palladium and a trivalent organic phosphorus compound, so that the produced N-carboxylate ions are stereo-selectively cyclized.

The process of the present invention will be further explained in detail.

In synthesizing an aryl halide compound or sulfonate compound employed as the starting material and represented by the formula (III):

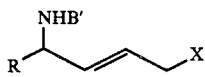 (III)

(wherein R is as defined above, X denotes a bromine atom, a chlorine atom, a paratoluenesulfonyloxy group or a methanesulofonyloxy group, and B' a BOC group, Z group or an aryloxycarbonyl group),
an a amino aldehyde easily obtained from -amino acid and having the general formula (IV):

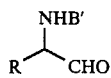 (IV)

(where R and B' are as defined above) is acted upon by a phospholane represented by a formula (V):

 (V)

(where R' is a lower alkyl group) and the resulting product is reduced to produce an aryl alcohol compound having the general formula (VI):

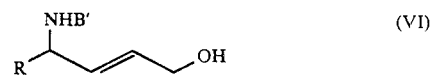 (VI)

(where R and B' are as defined above). When N-chorosuccinimide or N-bromosyocinimide succinate is caused to act on the produced aryl alcohol compound in the presence of triphenylphosphine, there is obtained an aryl halide compound according to the general formula (III) wherein X is a chlorine atom or a bromine atom. When paratoluene sulfonyl chloride or methanesulfonyl chloride is caused to act on the compound of the formula (VI), there is obtained a sulfonate compound according to the general formula (III) wherein X is a paratoluene sulfonyloxy group or a methanesulfonyloxy group.

By causing 1.5 to 2 equivalents of t-butyldimethylsilyl triflate, abbreviated to TBDMSOTF, t-butyl diphenylsilyl triflate or t-butyl dimethylsilane—palladium (II) catalyst to act on the compound (III) in the presence of a base, there is obtained a silyl carbamate derivative having the general formula (VII).

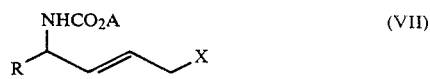 (VII)

(wherein R and X are as defined above) and A denotes a t-butyldimethylsilyl group.

By processing the compound (VII) with a fluorine ion containing reagent, a null- or divalent palladium compound and a trivalent organic phosphorus compound in the presence of an organic solvent, there is obtained a cyclic carbamate derivative according to the present invention having the general formula (VIII):

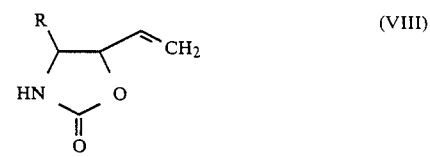 (VIII)

(wherein R is as defined above). It is noted herein that the aforementioned N-carboxylate ions are cyclized stereoselectively, with the group X acting as an eliminative group.

Any organic acid not taking part in the reaction may be employed, such as acetonitrile, dimethylacetamide, dimethylformamide, toluene, benzene, xylene or nitromethane. The reaction may be carried out at a temperature below room temperature, and preferably at 5° to 28° C. As the fluorine ion containing reagent employed in the reaction, tetraalkylammonium fluoride such as tetrabutylammonium fluoride or tetraisopropylammonium fluoride, silver fluoride, copper fluoride or boronated tetrafluoro silver, for example, are preferred. However, the reaction proceeds with the metal reagent, other than the fluorine ion containing reagent, such as trifluoromethane sulfonyl silver.

Although the reaction of cyclization proceeds without addition of nul- or divalent palladium compound or a trivalent organic phosphorus reagent, the rate of or a t-butyldiphenylsilyl stereo selectivity of the cyclization reaction is improved significantly by the addition of the null- or divalent palladium compound and a trivalent organic phosphorus compound.

As the null—or divalent palladium compounds, allyl palladium chloride (dimer), palladium acetate, palladium chloride, palladium bromide, palladium (II) acetyl acetonate, palladium sulfate, palladium trifluoroacetic acid, tetrakistriphenylphosphine palladium or palladium—carbon are preferred.

As the trivalent organic phosphorus reagent, trialkylphosphines such as triphenylphosphine or tributyl phosphine are preferred. Any group that may be eliminated by customarily employed $X^{\ominus}$ may be used as the group X, as mentioned above. However, chlorine or bromine atoms or paratoluenesulfonyloxy or methanesulfonyloxy groups commonly employed as synthetic means are most preferred.

By subjecting this compound (VIII) to a hydroboronating reaction in an etheric solvent, preferably in tetrahydrofuran, an alcohol compound is obtained which has a general formula (IX):

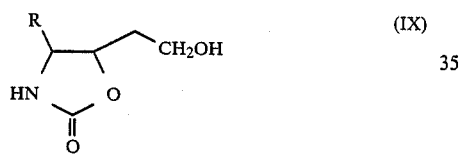

(wherein R has the same meaning as defined above). In carrying out the hydroboration reaction, a process is customarily employed which comprises reaction with boron compounds such as diborane, borane tetrahydrofuran complex, alkylborane or dialkylborane, followed by processing with aqueous hydrogen peroxide under basic conditions.

The boron compounds and bases may be enumerated by 9-borabicyclo[3.3.1]nonane and an aqueous sodium hydroxide.

After termination of the reaction, the organic solvent is distilled off under reduced pressure and the residual product is subjected to extraction with an organic solvent immiscible with water. The solvents used for extraction may be enumerated by esters of acetic acid, such as ethyl acetate and chlorine type solvents such as chloroform.

The extract solution is condensed and the obtained residual is dissolved in alcohol. To the resulting solution is added an aqueous solution of a base to hydrolyze a carbamate to produce an amino alcohol compound having the general formula (X):

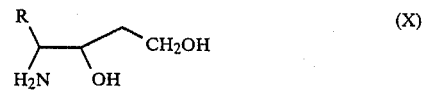

(wherein R has the meaning defined above).

The bases employed for this hydrolysis may be weak bases. For example, barium hydroxide, lithium hydroxide, sodium carbonate, potassium carbonate or sodium bicarbonate, are preferred. The reaction may be carried out at 60° to 100° C. for 10 to 40 hours.

After termination of the reaction, the reaction product may be liberated and refined by employing strong anionic exchange resins such as Dowex ® 50W×4 and weak bases.

As weak bases, ammonia and water are generally preferred.

The resulting product is condensed and an amino group of the obtained amino alcohol is treated with a conventional protecting reagent to produce a N-protected compound (XI):

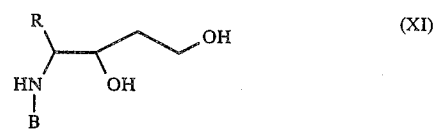

(wherein R and B have the meanings defined above). Any desired protective groups may be used, with the commonly used groups Boc and Z being preferred.

This compound is dissolved in a suitable solvent and oxidized by contacting with oxygen and using platinum oxide or rhodium oxide as the catalyst to produce protected statin and related compounds thereof having the general formula (I):

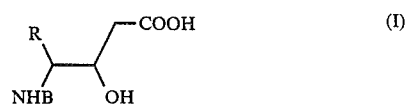

(wherein R and B have the meanings defined above).

The compound (III) employed as the starting material in the process of the present invention is not subject to racemation from α-amino acids, as confirmed by converting the compound (III) into an ester of α-methoxy-α-trifuloromethylphenyl acetic acid (MTPA).

The fourth and fifth positions of the cyclic carbamate derivative (VIII) most critical in the process of the present invention are threo types while the by-produced erythro type may be easily separated on recrystallization.

It has been confirmed that, by comparison with the physical data of the natural products, no racemation takes place in the course of the preparation of statin and related compounds from the compound (VIII).

EXAMPLES

The present invention will be explained further with reference to Examples and Comparative Examples. It should be noted that these Examples are given for the sake of illustration only and are not intended to limit the scope of the invention. In these Examples, s, d, m and br of the NMR spectrum data represent singlet, doublet, multiplet and broad, while the following abbreviations represent the following meanings:

MeOH: methanol
Boc: t-butoxycarbonyl group
t-Bu: t-butyl
MPTA: α-methoxy-α-trifluoromethylphenyl acetate group
PTLC: Preparative thin layer chromatography Si<t: t-butyldimethyl silyl group
28% NH₃: concentrated ammonia water (28%)

REFERENCE EXAMPLE 1

(4S)-4-N-(t-butoxycarbonyl)amino-6-methyl-2-ethyl heptenoate

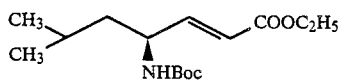

To a benzene solution (50 ml) of N-t-butoxycarbonyl-L-leucinal (3.0 g, 14 millimol $[\alpha]_D^{30} -26.0°$ (c=1.0, MeOH)) obtained by the conventional method was added to carboethoxymethylene triphenyl phosphorane (7.3 g, 21 millimol) and the resulting mixture was stirred at 25° C. for 30 minutes. The solvent was distilled off and the precipitates were subjected to silica gel column chromatography (ether/hexane=1/1). 3.8 g of the captioned compound was obtained in the form of a colorless oily substance. Yield: 96%.

REFERENCE EXAMPLE 2

(4S)-4-N-(t-butoxycarbonyl)amino-5-phenyl-2-ethyl pentenoate

From N-t-butoxycarbonyl-L-phenyl alaninal (2.0 g, 8.0 millimol $[\alpha]_D^{33} -26.7°$ (c=1.0 MeOH)) obtained by the conventional method, 2.5 g of the captioned compound was obtained in accordance with the method of the Reference Example 1. Yield: 98.5%.

REFERENCE EXAMPLE 3

(4S)-4-N-(t-butoxycarbonyl)amino-6-methyl-2-heptene-1-ol

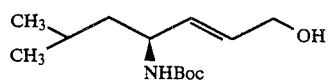

To 100 ml of a solution in methylene chloride of 3.8 g (13 millimol) of the compound of the Reference Example 1, cooled to −50° C., was added 1.81 ml (15 millimol) of a boron trifluoride ether complex salt under a nitrogen atmosphere, and the resulting mixture was stirred for 15 minutes. To the resulting mixed solution was added diisobutylaluminium hydride (1 mol hexane solution, 40.2 ml, 40 millimol) and the resulting solution was further stirred for two hours. To the resulting solution were added 6.9 ml (121 millimol) of acetic acid, 100 ml of ether, 5 ml of water and anhydrous magnesium sulfate. The resulting product was filtered and the solvent was distilled off under a reduced pressure. The resulting oily substance was subjected to a silica gel column chromatography (ether/hexane=2/1). 2.8 g of the captioned compound was obtained in the form of colorless prismatic crystals. Yield: 87%.

The product had the following physical properties: melting point, 82.0° to 83.0° C. (recrystallization from hexane); IR spectrum film (cm⁻¹), 3336, 1694, 1534; mass spectrum (m/z), 244 (M+1)⁺, 188, 170; ¹H NMR spectrum (60 MHz, CDCl₃), 0.93 (6H, d, J=6.0 Hz), 1.1 to 1.8 (3H, m), 1.45 (9H, s), 33.6 (1H, m), 3.60 (1H, m), 4.08 (2H, m), 4.80 (1H, d, J=8.0 Hz), 5.65 (2H, m); specific rotation, $[\alpha]_D^{30} -22.0°$ (c=1.0, MeOH).

REFERENCE EXAMPLE 4

(4S)-4-N-(t-butoxycarbonyl)amino-5-phenyl-2-pentene-1-ol

1.6 g of the captioned compound was obtained from 2.5 g (8.0 millimol) of the compound of Reference Example 2 as colorless needle crystals in accordance with Reference Example 3. Yield: 74%.

The product had the following physical properties: Melting point, 96.0° to 97.0° C. (with recrystallization from ether and hexane); IR spectrum (film, cm⁻¹), 3360, 1696, 1500; mass spectrum (m/z), 206, 186; ¹H NMR spectrum (100 MHz, CDCl₃), 1.40 (9H, s), 1.87 (brs 1H), 2.83 (2H, d, J=7.0 Hz), 4.06 (2H, brs), 4.5 (2H, m), 5.67 (2H, m), 7.2 (5H, m); specific rotation, $[\alpha]_D^{29} -4.8°$ (c=1.0, MeOH).

REFERENCE EXAMPLE 5

(4S)-4-N-(+)-methoxytrifluoro methyl phenyl acetamide-6-methyl-2 heptene-1-ol-(+) methoxy trifluoromethyl phenyl acetyl ester

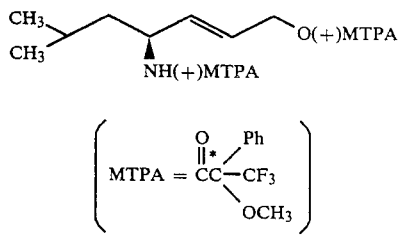

To 1 ml of a solution in methylene chloride of 20 mg of the compound of Reference Example 3 was added 1 ml of trifluoro acetic acid and the resulting mixture was stirred at 25° C. for 30 minutes. After the solvent had been distilled off under reduced pressure, the precipitates were diluted in 30 ml of water and processed by ion exchange resin column chromatography (Dowex 50W×4, 28% NH₃). The solvent was again distilled off under reduced pressure. The oily substance produced was dissolved in a mixed solution of 1 ml of pyridine and 1 ml of carbon tetrachloride. To the resulting solution was added 0.3 ml of a chloride of (+)−methoxy-trifluoromethyl phenyl acetic acid and the resulting product was stirred at 25° C. for three hours. The resulting product was admixed with water and extracted with ether, and the ether phase was dried over anhydrous magnesium sulfate. Then, after filtration, the solvent was distilled off under a reduced pressure. The produced oily substance was subjected to partition thin layer chromatography (ether/hexane=1/1) and 19 mg of the captioned compound was thereby obtained.

The produced captioned compound was in the form of a colorless oil substance, and from ¹H NMR (360 MHz), it was ascertained that the compound was not racemated.

¹H NMR (360 MHz CDCl₃), 0.93 (3H, d, J=7.0 Hz), 0.93 (3H, d, J=7.0 Hz), 1.3 to 1.7 (3H, m), 3.42 (3H, q,

J=1.0 Hz), 3.53 (3H, q, J=1.0 Hz), 4.57 (1H, m), 4.77 (2H, m), 5.67 (2H, m), 6.62 (1H, brd J=9.0 Hz), 7.3 to 7.6 (10H, m).

REFERENCE EXAMPLE 6

(4S)-4-N-(+)-methoxy trifluoromethyl phenyl acetoamide-5-phenyl-2-pentene-1-ol-(+)-methoxy trifluoromethyl phenyl acetic acid ester

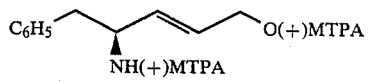

3 mg of the captioned compound was obtained from 3 mg of the compound of Reference Example 4 in accordance with Reference Example 5.

The compound was in the form of a colorless oily substance and, from $^1$H NMR (360 MHz), it was found not to have been racemated.

$^1$H NMR spectrum (360 MHz, CDCl$_3$), 2.82 (1H, dd J=14.0, 7.0 Hz), 2.94 (1H, dd, J=14.0, 7.0 Hz), 3.20 (3H, q, J=1.0 Hz), 3.50 (3H, q, J=10.0 Hz), 4.53 (2H, d, J=6.0 Hz), 4.84 (1H, d, d, d, J=8.0, 7.0, 7.0 Hz), 5.55 (1H, d, t, J=14.0, 6.0), 5.76 (1H, d, d, J=14.0, 6.0 Hz), 6.60 (1H, brd, J=8.0 Hz), 7.1–7.5 (15H, m).

REFERENCE EXAMPLE 7

(4S)-4-N-(t-butoxycarbonyl)amino-6-methyl-2-heptene-1-chloride

To 50 ml of a solution in methylene chloride of 2.3 g (9.3 millimol) of the compound of Rererence Example 3 were added 4.9 g (18.6 millimol) of triphenylphosphin and 1.9 g (14.0 millimol) of N-chlorosuccinimide under ice cooling. After raising the temperature to 25° C., the resulting mixture was stirred for 20 hours, and the solvent was distilled off. The oily substance produced was subjected to silica gel column chromatography (ether/hexane=1/5). 2.4 g of the captioned compound was obtained as a colorless oily substance. Yield: 100%.

The compound had the following physical properties: IR spectrum (film, cm$^{-1}$), 3348, 1698, 1522; mass spectrum (m/z), 204 (M-tBu)$^+$, 170 148; $^1$H NMR spectrum (60 MHz, CDCl$_3$), 0.91 (6H, d, J=6.0 Hz), 1.1–1.8 (3H, m), 1.44 (9H, s), 4.00 (2H, m), 4.15 (1H, m), 4.59 (1H, brd, J=8.0 Hz), 5.65 (2H, m); specific rotation, $[\alpha]_D^{28} -27.7°$ (c=1.0, MeOH).

REFERENCE EXAMPLE 8

(4S)-4-N-(t-butoxycarbonyl)amino-5-phenyl-2-pentene-1-chloride

1.2 g of the captioned compound was obtained as colorless prismatic crystals from 1.2 g (4.4 millimol) of the compound of Reference Example 4 in accordance with Reference Example 5. Yield: 94%.

The produced compound had the following physical properties: melting point, 68.0°–69.0° C. (recrystallization from hexane); IR spectrum (film, cm$^{-1}$), 3380, 1685, 1520; mass spectrum (m/z), 204 (M+1)-$^t$BuC$^+$, 178, 148; $^1$H NMR spectrum (100 MHz, CDCl$_3$), 1.42 (9H, s), 2.85 (2H, m), 4.02 (2H, m), 4.44 (2H, m), 5.70 (2H, m), 7.26 (5H, m); specific rotation, $[\alpha]_D^{33} -6.0°$ (c=1.0 MeOH).

REFERENCE EXAMPLE 9

(4S)-4-N-(t-butylmethylsilyloxycarbonyl)amino-6-methyl-2-heptene-1-chloride

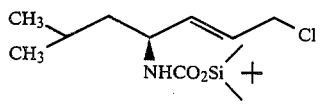

To 16 ml of a methylene chloride solution of 2.1 g (8.0 millimol) of the compound of Reference Example 7 were added 1.86 ml (16 millimol) of 2,6-lutidine and 2.75 ml (12 millimol) of t-butyldimethylsilyl-trifluoromethane sulfonate and the resulting mixture was stirred at 25° C. for 15 minutes under a nitrogen atmosphere and admixed with an aqueous solution of saturated ammonium chloride. Anhydrous magnesium sulfate was added to an organic layer obtained after extraction with ether and the resulting product was dried and filtered. After distilling off the solvent under a reduced pressure, 2.8 g of the captioned compound was obtained as a colorless oily substance.

The obtained compound had the following properties: IR spectrum (film, cm$^{-1}$), 3344, 1696, 1508; $^1$H NMR spectrum (60 MHz, CDCl$_3$), 0.25 (6H, s),0.92 (9H, s), 0.92 (6H, d, J=7.0 Hz), 1.1–1.9 (3H, m), 3.94 (2H, m), 4.15 (1H, m), 4.70 (1H, d, J=8.0 Hz), 5.65 (2H, m).

REFERENCE EXAMPLE 10

(4S)-4-N-(t-butyl dimethylsilyl oxycarbonyl)amino-5-phenyl-2-pentene-1-chloride

1.07 g of the captioned compound was obtained as a colorless oily substance from 760 mg (2.6 millimol) of the compound of Reference Example 8 in accordance with Reference Example 9.

The compound had the following properties: $^1$H NMR spectrum (100 MHz, CDCl$_3$), 0.24 (6H, s), 0.94 (9H, s), 2.86 (2H, d, J=7.0 Hz), 4.02 (2H, m), 4.2–4.8 (2H, m), 5.70 (2H, m), 7.0 to 7.0 (5H, m).

EXAMPLE 1

(4S, 5S)-4-isobutyl-5-vinyl-2-oxazolidone

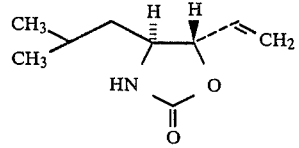

To 8 ml of an acetonitrile solution of 2.03 g (16 millimol) of silver fluoride, 420 mg (1.6 millimol) of triphenylphosphine and 145 mg (0.4 millimol) of allyl palladium chloride dimer was added 8 ml of an acetonitrile solution of 2.8 g (8.0 millimol) of a compound of Reference Example 9 and the resulting product was stirred at 25° C. for three hours under a nitrogen atmosphere. Ether and anhydrous magnesium sulfate were added to the product and, after filtration of the resulting mixture, the solvent was removed by distillation under reduced pressure. The obtained oily substance was subjected to silica gel column chromatography under a medium pressure (ether/hexane=2/1). In this manner, 950 mg of the captioned compound was obtained at a yield of 70%, and 62 mg of 4,5-cis isomer at a yield of 5%.

The obtained product was a colorless oily substance and had the following properties: IR spectrum (film, cm$^{-1}$), 3280, 1760, 1470, 1390; mass spectrum (m/z), 169 (M+), 141, 125, 112; $^1$H NMR spectrum (100 MHz, CDCl$_3$), 0.90 (3H, d, J=6.0 Hz), 0.92 (3H, d, J=6.0 Hz), 1.2–1.92 (3H, m), 3.58 (1H, dddd, J=6.5, 5.5, 5.5, 1.0 Hz), 4.50 (1H, dddd, J=6.5, 6.5, 1.0, 1.0 Hz), 5.28 (1H, ddd, J=10.5, 1.5, 1.0 Hz), 5.38 (1H, ddd, J=17.0, 1.5, 1.0 Hz), 5.90 (1H, ddd, J=17.0, 10.5, 6.5 Hz), 6.68 (1H, brs); specific rotation, $[\alpha]_D^{34}$ −76.4° (c=1.0, MeOH).

EXAMPLE 2

(4S, 5S)-4-phenylmethyl-5-vinyl-oxazolidone

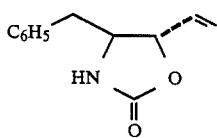

365 mg of a product was obtained from 1.07 g (2.6 millimol) of the captioned compound of Comparative Example 10 as a mixture of the captioned compound and 4,5-cis isomer thereof. The yield was 70%. From NMR, the 4,5-trans/cis ratio was determined to be 10/1. The yield was 70%. The pure product of the captioned compound was obtained by recrystallization from ether and hexane.

The product was in the form of colorless needle crystals and the melting point was 71.0°–72.0° C. (recrystallization from ether and hexane). IR spectrum (film, cm$^{-1}$), 3280, 1740, 1500; mass spectrum (m/z), 203 (M+), 160, 112; $^1$H NMR spectrum (100 MHz, CDCl$_3$), 2.87 (2H, d, J=7.0 Hz), 3.77 (1H, dt, J=7.0, 7.0 Hz), 4.64 (1H, dd, J=7.0, 7.0 Hz), 5.17 (1H, dd, J=10.0, 1.0 Hz), 5.22 (1H, dd, J=17.0, 1.0 Hz), 5.72 (1H, ddd, J=17.0, 10.0, 7.0 Hz), 6.62 (1H, s), 7.27 (5H, m); specific rotation, $[\alpha]_D^{34}$ −53.1° (c=1.0, MeOH).

EXAMPLE 3

(3S, 4S)-4-N-(t-butoxycarbonyl)amino-3-hydroxy-6-methyl-heptane-1-ol

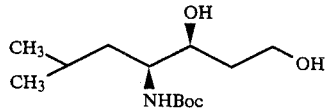

To 3 ml of a tetrahydrofurane solution of 59.0 mg (0.35 millimol) of the compound of Example 1 was added 2.1 ml (1.05 millimol) of a 0.5N 9-borabicyclo[3.3.1]nonane (9-BBN) hexane solution and the resulting mixture was stirred at 25° C. for 20 hours under a nitrogen atmosphere.

640 μl (10.8 millimol) of ethanol, 215 μl (1.3 millimol) of 6N aqueous solution of sodium hydroxide and 426 μl (3.8 millimol) of 30% aqueous hydrogen peroxide were added to the above mixture and the resulting product was stirred for a further thirty minutes and extracted with ethyl acetate. After addition of anhydrous magnesium sulfate to the obtained organic layer and drying, the solvent was distilled off under reduced pressure.

30 ml of ethanol and 6 ml of an aqueous solution of saturated barium hydroxide were added to the oily substance produced and refluxing was continued for thirty hours. After distilling off ethanol under reduced pressure and addition of 50 ml of water, the resulting product was subjected to ion exchange resin (Dowex-—50W×4, 28% NH$_3$ aqueous solution) and the disolvent was distilled off under reduced pressure.

To 5 ml of an obtained tetrahydrofuran solution of the amino diol form, 50 μl (0.35 millimol) of triethylamine and 122 μl (0.53 millimol) of di-t-butyldicarbonate were added and the resulting mixture was stirred at room temperature for twenty hours. The solvent was distilled off under a reduced pressure and the oily substance obtained was subjected to silica gel column chromatography (ethyl acetate/ether=1/5). 75 mg of the captioned compound was obtained as a colorless oily substance. Yield: 82%.

The obtained product was a colorless oily substance and had the following properties: IR spectrum (film, cm$^{-1}$), 3395, 1690, 1520; mass spectrum (m/z), 262 (M+1), 206, 186; $^1$H NMR spectrum (100 MHz, CDCl$_3$), 0.91 (6H, d, J=7.0 Hz), 1.43 (9H, s), 3.23 (1H, brs), 3.4–3.9 (5H, m), 4.82 (1H, d, J=9.0 Hz); specific rotation, $[\alpha]_D^{29}$ −76.4° (c=1.0, MeOH).

EXAMPLE 4

(3S, 4S)-4-N-(t-butoxycarbonyl)amino-3-hydroxy-5-phenyl-pentanol

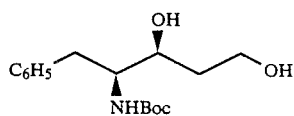

In accordance with Example 3, 117.6 mg (0.53 millimol) of the captioned compound was obtained as colorless needle crystal from 107.5 mg (0.53 millimol) of the compound of Example 2.

Melting point, 106.0°–108.0° C. (recrystallization from ether and hexane); IR spectrum (film, cm$^{-1}$), 3405, 1690, 1500; mass spectrum (m/z), 222 (M-$^t$BuO)+, 204, 164, 148; $^1$H NMR spectrum (100 MHz, CDCl$_3$), 1.41 (9H, s), 1.4–2.0 (2H, m), 2.84 (1H, brs), 2.88 (2H, d, J=7.0 Hz), 3.4–4.0 (5H, m), 5.02 (1H, d, J=9.0 Hz), 7.25 (5H, s); specific rotation, $[\alpha]_D^{29}$ −38.2° (c=1.0 MeOH).

EXAMPLE 5

(3S, 4S)-4-N-(t-butoxycarbonyl amino-3-hydroxy-6-methyl-heptanoic acid
(N-$^t$Boc statin)

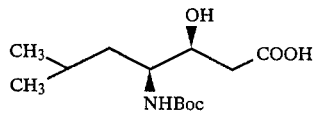

To 55 mg (0.24 millimol) of platinum oxide was added 3 ml of water and the resulting mixture was stirred for thirty minutes under a hydrogen atmosphere. To this suspension was added 2 ml of a dioxane solution of 63 mg (0.24 millimol) of the compound of Example 3 and after setting up oxygen atmosphere, the resulting mixture was stirred at 55° C. for thirty hours. After separation with addition of an aqueous solution of saturated sodium hydrogen carbonate and ether, setting the water layer portion to pH of 3 and extraction with ethyl acetate, the resulting organic layer was dried over anhydrous magnesium sulfate and the solvent was distilled off under reduced pressure. 40 mg of the captioned compound was obtained as colorless needle crystals. Yield: 60%.

Melting point, 118.0°–120.0° C. (recrystallization from ether and hexane) (value in literature, 118°–120° C.); IR spectrum (film, cm$^{-1}$), 2970, 1715, 1695, 1515; mass spectrum (m/z), 202 (M-$^t$BuO)+; $^1$H NMR spectrum (100 MHz, CDCl$_3$), 0.94 (6H, d, J=7.0 Hz), 1.46 (9H, s), 1.0–1.8 (3H, m), 2.56 (2H, d, J=7.0 Hz), 3.60 (1H, m), 4.02 (1H, m), 4.84 (1H, d, J=9.0 Hz), 6.30 (2H, brs); specific rotation, $[\alpha]_D^{34}$ −38.4° (c=0.5, MeOH). (value in literature: $[\alpha]_D^{24}$ −39.3° (c=1.5, MeOH); literature: B. E. Evans, Journal of Organic Chemistry, 47 3016 (1982).

EXAMPLE 6

(3S, 4S)-4-N-(t-butoxycarbonyl)amino-3-hydroxy-5-phenylpentanoic acid
(N-$^t$BOC AHPPA)

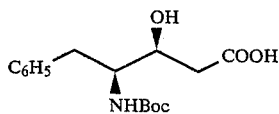

In accordance with Example 5, 44.4 mg of the captioned compound was obtained as colorless needle crystals from 76.5 mg (0.26 millimol) of the compound of Example 5. Yield: 55%.

Melting point, 151.0°–152.0° C. (recrystallization from chloroform and hexane); IR spectrum (film, cm$^{-1}$), 3350, 1715, 1515; mass spectrum (m/z), 253 [(M+1)-$^t$BU]+, 236, 218; $^1$H NMR spectrum (100 MHz, CDCl$_3$)/CD$_3$OD=10/1), 1.32 (9H, s), 2.36 (2H, m), 2.79 (2H, d, J=7.0 Hz), 3.6 (uperimposed on the 1H, DHO signal), 3.90 (1H, m), 7.17 (5H, s); specific rotation, $[\alpha]_D^{30}$ −37.5° (c=0.54, MeOH); [value in lieterature, −37.0° c=1.1 MeOH. (literature: D. H. Rich, J. Med. Chem.) (1980), 23, 27].

What is claimed is:
1. A process for producing statin having the general formula:

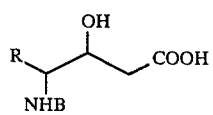

(wherein R is a C1 to C6 alkyl group, a phenyl group or a C7 to C8 phenylalkyl group and B is a protective group for an amino group) characterized by the steps of treating a silyl carbamate having the formula

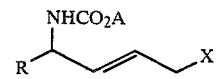

(wherein A is a t-butyldimethylsilyl or t-butyldiphenylsilyl group: X is a bromine atom, a chlorine atom, paratoluenesulfonyloxy or methanesulfonyloxy group and R is as defined above);
with a fluorine-containing ionic reagent in the presence of a null-valent or di-valent palladium and a trivalent organic phosphorus compound to form a cyclic carbamate having the general formula:

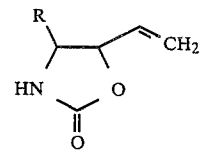

(wherein R has the meaning as defined above);
subjecting said cyclic carbonate to a hydroborating reaction, basic oxidation cracking and protection of the amino group to produce a diol having the general formula:

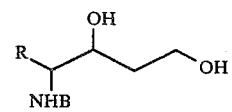

(wherein R and B have the meaning as defined above) and further oxidizing said diol.
2. The process according to claim 1 wherein the null- or di-valent palladium is palladium acetate, palladium chloride, palladium bromide, sodium palladium chloride Na$_2$PdCl$_4$), aryl palladium chloride, dimer, tetrakistriphenyl phosphine palladium or palladium carbon.
3. The process according to claim 1 wherein the fluorine-containing ionic reagent is tetraalkylammonium fluoride, silver fluoride, copper fluoride, sodium fluoride, potassium fluoride, cesium fluoride or silver tetrafluoroboride.
4. The process according to claim 1 wherein the reagent employed in the hydroborating reaction is diborane-aqueous hydrogen peroxide, alkylborane-aqueous hydrogen peroxide or dialkylborane-aqueous hydrogen peroxide.
5. The process according to claim 1 wherein the reagent for hydrolysis is barium hydroxide, sodium carbonate, potassium carbonate, sodium bicarbonate, potassium hydroxide or lithium hydroxide.
6. The process according to claim 1 wherein the oxidant is rhodium oxide-oxygen or platinum oxide-oxygen.
7. The process according to claim 1 wherein the organic phosphorus compound is triphenyl phosphine or tributyl phosphine.
8. The process according to claims 1, 2 or 3 wherein the cyclic carbamate having the general formula:

15
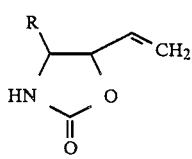
(wherein R is C1 to C6 alkyl group, phenyl group or a C7 to C8 phenylalkyl group) is an optically active substance.
* * * * *
16
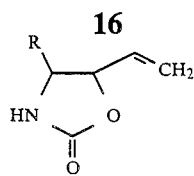
(wherein R is C1 to C6 alkyl group, phenyl group or a C7 to C8 phenylalkyl group) is an optically active substance.
* * * * *